United States Patent [19]

Bauman

[11] 4,059,687

[45] Nov. 22, 1977

[54] ESTER SUBSTITUTED DIBIGUANIDES AND NON-TOXIC ANTIMICROBIAL COMPOSITIONS THEREOF

[75] Inventor: Robert Andrew Bauman, New Brunswick, N.J.

[73] Assignee: Colgate Palmolive Company, New York, N.Y.

[21] Appl. No.: 745,511

[22] Filed: Nov. 26, 1976

[51] Int. Cl.$^2$ .................. A01N 9/24; A61K 7/22; C07C 129/16
[52] U.S. Cl. ..................................... 424/54; 424/310; 560/34
[58] Field of Search ..................... 260/471 R, 565; 424/310, 54

[56] References Cited

U.S. PATENT DOCUMENTS

| | | | |
|---|---|---|---|
| 2,684,924 | 7/1954 | Rose et al. | 260/565 X |
| 2,690,455 | 9/1954 | Kaiser et al. | 260/565 |
| 2,863,919 | 12/1958 | Birtwell et al. | 260/565 |
| 3,183,230 | 5/1965 | Shapiro et al. | 260/565 X |
| 3,794,685 | 2/1974 | Diamond et al. | 260/565 |

Primary Examiner—Richard L. Raymond
Attorney, Agent, or Firm—Robert L. Stone; Murray M. Grill; Herbert S. Sylvester

[57] ABSTRACT

Novel dibiguanides containing an ester substituent on the terminal phenyl radical and free of the presence of, or the tendency to form, toxic substances; the process of preparing said dibiguanides, and compositions containing an effective antimicrobial amount of said dibiguanides admixed with a pharmaceutical carrier.

9 Claims, No Drawings

ESTER SUBSTITUTED DIBIGUANIDES AND NON-TOXIC ANTIMICROBIAL COMPOSITIONS THEREOF

Dibiguanides (bis-biguanides) were investigated by ICI (Imperial Chemical Industries, Limited) as antimicrobials and Chlorhexidine was selected as the best, as reported in the British Journal of Pharmacology 9 (1954) pages 192-196. The compounds tested had a terminal phenyl, chlorophenyl, dichlorophenyl, hydroxyphenyl, carboxyphenyl, methoxyphenyl, diethyl groups. It was found that substituents other than chlorine markedly depressed the bacteriostatic activity of the dibiguanides.

The chemical configuration for Chlorhexidine is:

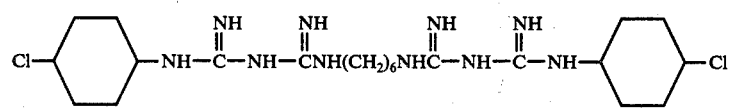

These and additional dibiguanides wherein the chlorine on the phenyl group is replaced by other halogens or by alkyl, alkoxy or nitro groups and the phenyl is attached directly or through an alkylene group to the biguanide nucleus are described in U.S. Pat. Nos. 2,684,924 and 2,683,919. The ethylene bis-aryl biguanides are described in U.S. Pat. No. 2,690,455. Dibiguanides wherein an ethyl hexyl radical is the terminal group attached to the biguanide nucleus in oral compositions is disclosed in U.S. Pat. Nos. 3,562,385 and 3,887,712. Related analogs of Chlorhexidine wherein the terminal phenyl group has a trifluoromethyl substituent is disclosed in the Journal of Medicinal Chemistry 1973 Vol. 16 No. 6 pages 732 and 733.

Although Chlorhexidine has been found to be an effective antibacterial agent against dental plaque, it is made from p-chloroaniline and the final product will contain small amounts of this reactant, which is a toxic substance. The British Pharmacopeia sets a limit of 0.05% p-chloroaniline. In addition, solutions of Chlorhexidine hydrolyze on standing to form additional amounts of p-chloroaniline.

In accordance with instant invention, it has been found that dibiguanides having a lower alkyl ester substituent on the terminal phenyl radical exhibit superior antimicrobial activity, and are free of toxic substances, with maximum activity when the ester is butyl or pentyl. More specifically, instant novel compounds are free of toxic substances such as p-chloroaniline, since said toxic substance does not constitute a reactant in the synthesis of the present novel dibiguanides.

Accordingly, it is an object of this invention to provide safe and effective antimicrobial agents for the control of dental plaque, caries, calculus, and periodontal disease.

Another object of this invention is to provide novel antimicrobial dibiguanides free of either the presence of, or the tendency to form toxic substances.

Accordingly, the present invention relates to non-toxic oral compositions and to novel dibiguanide compounds represented by the general formula:

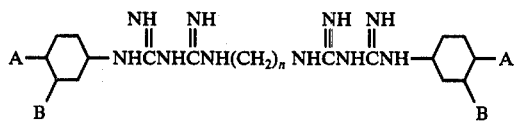

wherein one of A and B is hydrogen and the other is the ester radical

and R is an alkyl group containing 1-8 carbon atoms, and $n$ is an integer from 5 to 12. These compounds may be in the form of the free base or salts formed with acids such as HCl, HBr, HI, HF, $H_2SO_4$, $CH_3COOH$, gluconic acid, $H_2PO_3F$, $H_3PO_4$. These compounds and oral compositions containing said dibiguanide compounds are free of toxic substances and possess superior antimicrobial, antiplaque, anticaries and anticalculus activity, with maximum activity where R has 4-5 carbon atoms.

The method of preparing the non-toxic dibiguanides of instant invention comprises reacting the acid salts, preformed or made in situ, of a $C_1$-$C_8$ alkyl aminobenzoate such as its hydrochloride salt with a polymethylene-bis (3-cyano-guanidine). If desired the acid salt may be neutralized to form the free base. The reaction is preferably conducted in the presence of a suitable organic solvent at the elevated temperatures, preferably at the boiling point of said solvent. Suitable solvents include propanol, 2-propanol, ethanol, butanol, ethoxyethanol, methanol and the like. When utilizing the preferred hydrochloride salt of the alkyl aminobenzoate, the resultant product is the acid addition salt of the dibiguanide, which can be neutralized with an alkali, such as sodium hydroxide to give the free dibiguanide.

The reaction is generally complete in less than 2 hours after heating is begun, particularly under reflux conditions. The reaction mixture usually sets into a solid mass and the dibiguanide is recovered by filtration and dried to a powder on a steam bath or by other suitable drying means. This powder may be purified by recrystallizing from water or any suitable alcohol. The dibiguanide salt may be converted to the free base and thence into any desired acid addition salt thereof by the addition of an equivalent amount of an acid selected from the group consisting of HCl, HBr, HI, HF, $H_2SO_4$, $CH_3COOH$, gluconic acid, $H_2PO_3F$ and $H_3PO_4$ (2 moles acid per mole dibiguanide). It has been found that the acetate salts are more water soluble than the hydrochloride salts.

The proportions of reactants are not critical, but it is preferred to use at least 2 moles or an excess of the alkyl aminobenzoate reactant per mole of the bis-guanidine reactant. Two moles of the aminobenzoate reactant will react with one mole of the bis-guanidine reactant to form one mole of the dibiguanide. An excess of the aminobenzoate reactant has no adverse affect on the reaction nor on the final product, since neither the alkyl aminobenzoate nor the aminobenzoic acid formed upon hydrolysis, are toxic and are even used medicinally.

The following examples illustrate the manner in which compounds of this invention are prepared:

EXAMPLE 1

Preparation of N,N''-bis(4-ethoxycarbonylphenyl)-3,12-diimino-2,4,11,13-tetraazatetradecanediimidamide dihydrochloride:

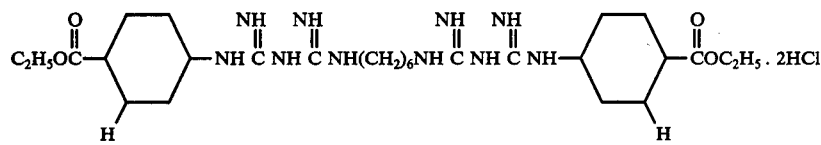

A mixture of 4.0 g (20 moles) ethyl p-aminobenzoate hydrochloride, 2.25g (9 moles) 1,6-hexanebis(3'-cyanoguanidine), and 15 ml 2-propanol was brought quickly to boiling and stirred under reflux for 10 minutes. The reaction mixture which set to a solid mass was transferred to a funnel and washed with hot 2-propanol. The washed product was dried on a steam bath and 4.1g (70% of theoretical yield) of a white powder was recovered. After recrystallizing from water, a microcrystalline powder having a melting point of 235°–7° C was recovered. Analysis for $C_{28}H_{40}N_{10}O_4 2HCl$:

|  | Calculated | Found |
|---|---|---|
| chlorine | 10.72 | 10.75 |

EXAMPLES 2–11

The following homologs utilizing the same bis-guanidine reactant but varying the benzoate reactant were prepared in accordance with the method of Example 1:

| Ex. | A | B | M.P. ° C | Ionic Cl, % Calcd | Found |
|---|---|---|---|---|---|
| 2 | $CH_3OCO$ | H | 261–1.5* | 11.34 | 11.27 |
| 3 | n-$C_3H_7OCO$ | H | 246–7* | 10.40 | 10.32 |
| 4 | i-$C_3H_7OCO$ | H | 238–40 | 10.40 | 10.23 |
| 5 | n-$C_4H_9OCO$ | H | 244–6* | 9.99 | 9.90 |
| 6 | n-$C_5H_{11}OCO$ | H | 236–7* | 9.61 | 9.44 |
| 7 | n-$C_6H_{13}OCO$ | H | 187–9 | 9.26 | 9.36 |
| 8 | n-$C_8H_{17}OCO$ | H | 194–6 | 8.63 | 8.79 |
| 9 | H | $CH_3OCO$ | 219–21* | 11.34 | 11.20 |
| 10 | H | i-$C_3H_7OCO$ | 222–4* | 10.40 | 10.39 |
| 11 | H | n-$C_4H_9OCO$ | 205–7* | 9.99 | 10.00 |

*recrystallized from alcohol or water

The process described in Example 1 may be varied by using other suitable solvents such as ethanol, butanol, ethoxyethanol, or methanol or no solvent and the temperature varied according to the boiling point of the solvent used. Other dibiguanide compounds may be prepared by utilizing different guanidine reactants such as 1,5-pentanebis(3'-cyano-guanidine); 1,7-heptanebis(3'-cyano-guanidine); 1,8-octanebis(3-cyano-guanidine); 1,9-nonanebis(3'-cyano-guanidine); 1,10-decanebis(3'-cyano-guanidine); 1,11-undecanebis(3'-cyano-guanidine); 1,12-dodecanebis(3'-cyano-guanidine). Similarly, the aminobenzoate reactant may be of an acid salt other than the hydrochloride, inclusive of other halide acid salts or the phosphate salts, or the sulfate or the gluconate or the acetate salts.

It has been observed that the compounds generally described by the foregoing formula are particularly effective against gram positive organisms such as *Staphylococcus aureus, Streptococcus sanguis* and *Streptococcus mutans;* gram negative organisms such as *Pseudomonas aeruginosa* and *Escherichia coli;* and against fungi, such as *Candida alibicans* (yeast) and *Trichophyton mentogrophytes* and *Aspergillus niger* (mold). Compounds wherein A or B is a carboxyl radical in lieu of instant alkyl ester radical are substantially devoid of antibacterial activity.

The anti-microbial nature of the instant novel non-toxic compounds was shown by a standard test tube serial dilution test in which an appropriate number of test tubes of broth containing decreasing concentrations of the test agent was innoculated with the test organism (0.1% in ethyl alcohol). After a suitable period of incubation, the tubes were examined for the presence or absence of growth. The activity of the test agent was the lowest concentration which inhibited the growth of the organism and is expressed as the minimal inhibitory concentration in $\mu$ gm/ml. As shown in the following table of antimicrobial data, the dibiguanides of this invention are active against a variety of micro-organisms with maximum activity with a butyl and pentyl ester substituent on the phenyl radical.

TABLE I

Minimum Inhibitory Concentration (μgm/ml)

| A | B | Gram Positive | | | Gram Negative | | Yeast | | Mold |
|---|---|---|---|---|---|---|---|---|---|
|   |   | S. aureus | Strep. mutans | Strep. sanguis | Ps. aeruginosa | E. coli | C. albicans | T. ment | A. niger |
| Cl (Chlorhexidine hydrochloride) | H | .19 | < .05 | 6.25 | 12.5 | .78 | 3.12 | 1.56 | 25 |
| COOH | H | 10.0 | 25. | 100 | 50 | 100 | 100 | 100 | 100 |
| $CH_3OCO$ | H | 6.25 | 1.56 | 50 | 50 | 25 | 25 | 12.5 | 100 |
| $C_2H_5OCO$ | H | .78 | .39 | 25 | 25 | 1.56 | 12.5 | 12.5 | 100 |
| $C_3H_7OCO$ | H | .19 | < .05 | 3.12 | 25 | 1.56 | 3.12 | 3.12 | 100 |
| $C_4H_9OCO$ | H | 0.1 | < .05 | .78 | 12.5 | 1.56 | 0.78 | 12.5 | 50 |
| $C_5H_{11}OCO$ | H | .39 | < .05 | .19 | 50 | 25 | 0.39 | 25 | 50 |

TABLE I-continued

| | | \multicolumn{8}{c}{Minimum Inhibitory Concentration (μgm/ml)} |
|---|---|---|---|---|---|---|---|---|---|
| $C_6H_{13}OCO$ | H | .39 | .39 | .39 | 50 | 6.25 | 0.39 | 12.5 | 100 |
| $C_8H_{17}OCO$ | H | 1.56 | 1.56 | 25 | 50 | 12.5 | 12.5 | 25 | 100 |
| H | $CH_3OCO$ | 3.12 | 1.56 | 100 | 50 | 12.5 | 25 | 12.5 | 100 |
| H | $(CH_3)_2CHOCO$ | .19 | 0.1 | 12.5 | 50 | 3.12 | 3.12 | 12.5 | 50 |
| H | $C_4H_9OCO$ | <.05 | <.05 | 1.56 | 12.5 | .78 | .39 | 6.25 | 50 |
| $(CH_3)_2CHOCO$ | H | .19 | 0.1 | 6.25 | 25 | 1.56 | 1.56 | 6.25 | 50 |

A—⟨ring with B⟩—NH C(=NH) NH C(=NH) NH(CH$_2$)$_6$NH C(=NH) NH C(=NH) NH—⟨ring with B⟩—A . 2CH$_3$COOH

| | | | | | | | | | |
|---|---|---|---|---|---|---|---|---|---|
| $CH_3OCO$ | H | 3.12 | 25 | 50 | 25 | 50 | 25 | 25 | 100 |
| Cl (Chlorhexidine) | H | 0.19 | <0.05 | 3.12 | 1.56 | 0.19 | 1.56 | 3.12 | 25 |
| $C_4H_9OCO$ | H | .05 | <.05 | .78 | 25 | 3.12 | .78 | 0.19 | 100 |

These dilution tests evidence the effectiveness of compounds of the invention against bacteria and fungi not possessed by the carboxy substituted phenyl radical. The antimicrobial effectiveness of instant novel compounds favorably compare to Chlorhexidine, and eliminate the toxic p-chloroaniline normally found in the Chlorhexidine product.

When used against bacteria or fungi, compounds of the instant invention may be applied directly to the surface to be protected or may be dissolved in a pharmaceutical carrier. Typically, an effective amount, e.g., 0.025 to about 10% by weight of the compound, is included in an inert carrier and a dispersing or surface-active agent. Alternatively, an effective amount, e.g., 0.025 to about 10% by weight may be incorporated into a solid carrier which may be inert, such as talc, clay, diatomaceous earth, flour, etc.

When compounds of the instant invention are intended for use in compositions which reduce formation of caries and inhibit the formation of oral plaque and calculus, and in the treatment of periodontal disease, they are typically incorporated in oral preparations in effective amounts up to about 5% by weight, preferably .025–1% and most preferably 0.05–0.5% by weight of the oral preparations. Typically, the oral preparation is a dentifrice, such as dental cream, tablet or powder, containing as a vehicle about 20–95% by weight of a water-insoluble polishing material, preferably including water-insoluble phosphate such as dicalcium phosphate, tricalcium phosphate, trimagnesium phosphate. The dentifrice may also include water; binders such as glycerine, sorbitol, propylene glycol 400; detergents; gelling agents such as Irish moss and sodium carboxy methyl cellulose; additional antibacterial agents; coloring or whitening agents; preservatives; silicones; chlorophyll compounds, additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 12

| Dental Cream | % |
|---|---|
| N, N''-bis (4-Ethoxycarbonylphenyl) -3, 12- diimino-2, 4, 11, 13- tetraazatetradecanediimidamide dihydrochloride | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |

*Tween 80-Polyoxyethylene (20 moles ethylene oxide) sorbitan monooleate.

EXAMPLE 13

0.50% of the butyl ester, [-bis(4-Butyloxycarbonylphenyl)-], was used in lieu of the ethyl ester in Example 12.

EXAMPLE 14

0.50% of the pentyl ester, [-bis(4-Pentyloxycarbonylphenyl)], was used in lieu of the ethyl ester of Example 12.

EXAMPLE 15

| Mouthwash | % |
|---|---|
| N, N''-bis(3-Methoxycarbonylphenyl)-3, 12-dimino-2, 4, 11, 13-tetraazatetradecanediimidamide acetate | 0.025 |
| Nonionic detergent (Pluronic F-68)* | 1.00 |
| Ethyl alcohol (containing flavor) | 15.00 |
| Glycerine | 10.00 |
| Saccharin | 0.02 |
| Water | 73.955 |

*Block polymer of 80% polyoxyethylene and 20% polyoxypropylene.

EXAMPLE 16

0.05% of N,N''-bis(3-Isopropoxycarbonylphenyl)-3,12-diimino-2,4,11,13-tetraazatetradecanediimidamide dihydrochloride was substituted for the dibiguanide of Example 15 and the water content was adjusted accordingly.

EXAMPLE 17

0.05% of N,N''-bis(4-Octyloxycarbonylphenyl)-3,12-diimino-2,4,11,13-tetraazatetradecanediimidamide dihydrochloride was used in lieu of the dibiguanide of Example 15 and the water content was adjusted accordingly.

EXAMPLE 18

0.05% of the diacetate salt of the dibiguanide having a dibutyl ester substituent on the terminal phenyl radicals was used in lieu of the dibiguanide of Example 15.

A preferred ingredient of instant composition is a non-ionic organic surfactant which provides increased prophylactic action, assists in achieving thorough and complete dispersion of instant compositions throughout the oral cavity and renders instant compositions more cosmetically acceptable. The non-ionic surfactant imparts to the composition, detersive and foaming properties as well as maintains the flavoring materials in solution (i.e., solubilizes flavor oils). In addition, the non-ionics are completely compatible with the dibiguanide compounds of this invention, thereby providing for a stable, homogeneous composition of enhanced anti-bacterial, anti-caries, anti-plaque, and anti-calculus activity.

The nonionic organic surface compounds which are contemplated are commercially known and comprise the water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, mercaptans, sulphonamides, etc. The ethylene oxide condensates with higher alkyl phenols represent a preferred class of nonionic compounds. Usually the hydrophobic moiety should contain at least about 6 carbon atoms, and preferably at least about 8 carbon atoms, and may contain as many as about 50 carbon atoms or more. The amount of alkylene oxide will vary considerably depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like may also be used or substituted in part for the ethylene oxide. Other nonionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other nonionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of nonionic products are the oxyalkylated higher aliphatic alcohols. The fatty alcohols should contain at least 6 carbon atoms, and preferably at least 8 carbon atoms. The most preferred alcohols are lauryl, myristyl, cetyl, stearyl and oleyl alcohols and the said alcohols should be condensed with at least about 6 moles of ethylene oxide, and preferably about 10 to 30 moles of ethylene oxide. A typical nonionic product is oleyl alcohol condensed with 15 moles of ethylene oxide. The corresponding alkyl mercaptans when condensed with ethylene oxide are also suitable in the compositions of the present invention.

The amount of non-ionic may generally be varied from about 0.2 – 3.0% by weight of the total formulation, depending on the specific nature of the non-ionic utilized as well as on the amounts and nature of the other ingredients in the oral formulation.

Although this invention has been described with reference to specific examples, it will be apparent to one skilled in the art that various modifications may be made thereto which fall within its scope.

I claim:

1. A dibiguanide compound free of toxic substances having the structural formula:

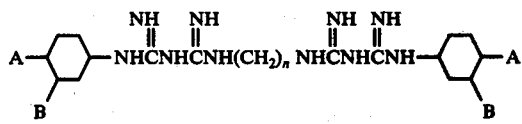

wherein one of A and B is hydrogen and the other is the ester radical

and R is an alkyl group containing 1–8 carbon atoms and $n$ is an integer from 5 to 12; and the acid salts thereof selected from the group consisting of HCl, HBr, HI, HF, $H_2SO_4$, $CH_3COOH$, gluconic acid, $H_2PO_3F$ and $H_3PO_4$.

2. A compound in accordance with claim 1 wherein $n$ is 6.

3. A compound in accordance with claim 1 wherein A is an ester radical and B is hydrogen.

4. A compound in accordance with claim 1 wherein B is an ester radical and A is hydrogen.

5. A compound in accordance with claim 1 having the formula N,N''-bis(4-butyloxycarbonylphenyl)-3,12,diimino-2,4,11,13-tetraazatetradecanediimidamide dihydrochloride.

6. A compound in accordance with claim 1 having the formula N,N''-bis(4-pentyloxycarbonylphenyl)-3,12,diimino-2,4,11,13,-tetraazatetradecanediimidamide.

7. A compound in accordance with claim 1, having the formula N,N''-bis(4-butyloxycarbonylphenyl)-3,12-diimino-2,4,11,13-tetraazatetradecanediimidamide diacetate.

8. A non-toxic composition containing an effective antimicrobial amount of the compound defined in claim 1 admixed with a pharmaceutical carrier.

9. A non-toxic composition containing an effective antimicrobial amount of the compound defined in claim 1 admixed with an oral preparation.

* * * * *